US012678210B2

(12) United States Patent
Carnemolla et al.

(10) Patent No.: US 12,678,210 B2
(45) Date of Patent: Jul. 14, 2026

(54) CRYOGENIC DEVICE AND METHOD FOR TREATMENT OF RHINITIS

(71) Applicant: 32 Surgical, LLC, Palm Beach Gardens, FL (US)

(72) Inventors: Anthony Carnemolla, Palm Beach Gardens, FL (US); Matthew J. Nalipinski, Livermore, CA (US); Agustin Arrieta, Pinecrest, FL (US)

(73) Assignee: 32 Surgical, LLC, Palm Beach Gardens, FL (US)

( * ) Notice: Subject to any disclaimer, the term of this patent is extended or adjusted under 35 U.S.C. 154(b) by 199 days.

(21) Appl. No.: 18/431,722

(22) Filed: Feb. 2, 2024

(65) Prior Publication Data

US 2025/0248754 A1 Aug. 7, 2025

(51) Int. Cl.
*A61B 18/02* (2006.01)
*A61B 17/34* (2006.01)
*A61B 18/00* (2006.01)

(52) U.S. Cl.
CPC .. *A61B 18/0218* (2013.01); *A61B 2017/3454* (2013.01); *A61B 2018/00095* (2013.01); *A61B 2018/00101* (2013.01); *A61B 2018/00327* (2013.01); *A61B 2018/00577* (2013.01); *A61B 2018/0212* (2013.01)

(58) Field of Classification Search
CPC .......... A61B 2018/00005; A61B 2018/00095; A61B 2018/00101; A61B 2018/00327; A61B 2018/00577; A61B 18/02; A61B 2018/0212; A61B 18/0218; A61B 2018/0231; A61B 2018/0262; A61F 2007/0006
See application file for complete search history.

(56) References Cited

U.S. PATENT DOCUMENTS

| | | | |
|---|---|---|---|
| 9,687,288 B2 | 6/2017 | Saadat | |
| 10,512,498 B2 | 12/2019 | Saadat | |
| 2017/0231474 A1* | 8/2017 | Saadat | A61B 1/0625 |
| | | | 600/107 |
| 2018/0125560 A1* | 5/2018 | Saadat | A61B 18/02 |
| 2019/0336196 A1* | 11/2019 | Wolf | A61N 1/403 |
| 2020/0205884 A1* | 7/2020 | Wolf | A61M 25/0084 |
| 2022/0233832 A1 | 7/2022 | Fahey et al. | |
| 2022/0257298 A1 | 8/2022 | Fox et al. | |

(Continued)

*Primary Examiner* — Bradford C. Blaise
(74) *Attorney, Agent, or Firm* — Crockett & Crockett, PC; K. David Crockett, Esq.

(57) ABSTRACT

Devices and methods for more effective cryoablation of a posterior nasal nerve. The cryoablation tip of the device is paddle-shaped, with broad, flat, overall rectangular outline with notches on the sides to create a metacentric outline. One side of the cryoablation tip is conductive, while the opposing side is highly non-conductive. Corner portions of the tip are also non-conductive. Intermediate portions of the side-edge surfaces conductive, and are configured as recesses or notches in the side edge. In use, the system will be inserted into the nasal cavity of a patient, with conductive surfaces of the cryoablation tip disposed in contact with portions of the turbinate lining overlying a posterior nasal nerve, and operated to cool those portions to ablate the posterior nasal nerve. The insulative portion of the cryoablation tip protects remaining surrounding tissue from cryoablation.

11 Claims, 8 Drawing Sheets

(56)　　　　　References Cited

U.S. PATENT DOCUMENTS

| 2022/0313484 | A1 | 10/2022 | Fahey et al. | |
| 2023/0069123 | A1* | 3/2023 | Soykan | A61B 18/02 |
| 2023/0248411 | A1* | 8/2023 | Fox | A61B 90/37 |
| | | | | 606/21 |
| 2024/0050143 | A1* | 2/2024 | Wolf | A61B 18/1206 |

* cited by examiner

CRYOGENIC DEVICE AND METHOD FOR TREATMENT OF RHINITIS

FIELD OF THE INVENTIONS

The inventions described below relate to the field of cryosurgical treatment for chronic rhinitis.

BACKGROUND OF THE INVENTIONS

Persistent runny nose, or chronic rhinitis, is a condition characterized in watery rhinorrhea, nasal congestion and postnasal drip. There are multiple causes of chronic rhinitis including allergies, exposure to irritants and structural and physiological abnormalities in the nose. These conditions result in inflammation of the nasal cavity activating a parasympathetic response via preganglionic fibers from the Vidian nerve and postganglionic stimulation of nasal mucosal cells by the Posterior Nasal Nerve.

Cryogenic ablation of the posterior nasal nerves in the mucosa anterior and posterior to the inferior attachment of the middle turbinate has been proposed as a treatment for chronic rhinitis. With currently proposed cryogenic end effectors, it is difficult to apply cryogenic cooling to the targeted anatomy overlying the posterior nasal nerves, specifically the posterior portion of the posterior nasal nerve which sits behind the middle turbinate attachment. The poor fit of the currently proposed cryogenic end effectors with the anatomy of the middle turbinate means that multiple applications of the cryogenic cooling through the end effector are required to ablate the posterior nasal nerve(s). This leads to increased procedure time, patient discomfort, and potential for greater collateral tissue damage which has been documented to lead to complications and/or side effects. Prior art cryoablation tools such as the CLARIFIX® cryotherapy device sold by Stryker (described in U.S. Pat. No. 9,687, 288) includes a paddle-shaped balloon which expands when cryogen is forced into the balloon. The CLARIFIX® cryotherapy device exhausts injected cryogen through the balloon walls and into the nasal cavity.

SUMMARY

The devices and methods described below provide for more effective cryoablation of a posterior nasal nerve. The device includes a cryogen source, a handle (which may be housed in the handle), a shaft extending from the handle, and a cryoablation tip configured for application of cryogenic cooling to the nasal cavity wall of the middle meatus and the posterior attachment of the turbinate. The cryoablation tip is generally paddle-shaped, with broad, flat, overall rectangular outline with notches on the sides to create a "metacentric" outline. One broad side of the cryoablation tip is highly thermally conductive, while the opposing broad side of the cryoablation tip is highly thermally insulative (non-conductive). Corner portions of the side-edge surfaces of the tip are also highly thermally insulative (non-conductive). Intermediate portions of the side-edge surfaces (between the corners) are thermally conductive, and are configured as recesses or notches in the side edge. The insulative side comprises a body including an insulative surface corresponding to the first broad surface, projections on the corners configured create a space to hold the structure that comprises the opposing conductive broad side, and notches in the side edge to match notches in the side edge of the opposing conductive broad side. In use, the system will be inserted into the nasal cavity of a patient, with conductive surfaces of the cryoablation tip disposed in contact with portions of the turbinate lining overlying a posterior nasal nerve or branches of the posterior nasal nerve, and operated to cool those portion to ablate the posterior nasal nerve. The notches allow the cryoablation tip to be seated toward the posterior end of the middle turbinate to contact areas of the lateral nasal wall in the meatus of the middle turbinate and posterior to (and perhaps superior to) the middle turbinate at the same time. The distal surface may be used to treat an anteriorly facing surface of a ridge extending inferiorly from the posterior and of the middle turbinate. The insulative portion of the cryoablation tip protects remaining surrounding tissue from cryoablation.

DETAILED DESCRIPTION OF THE INVENTIONS

Figure 1:
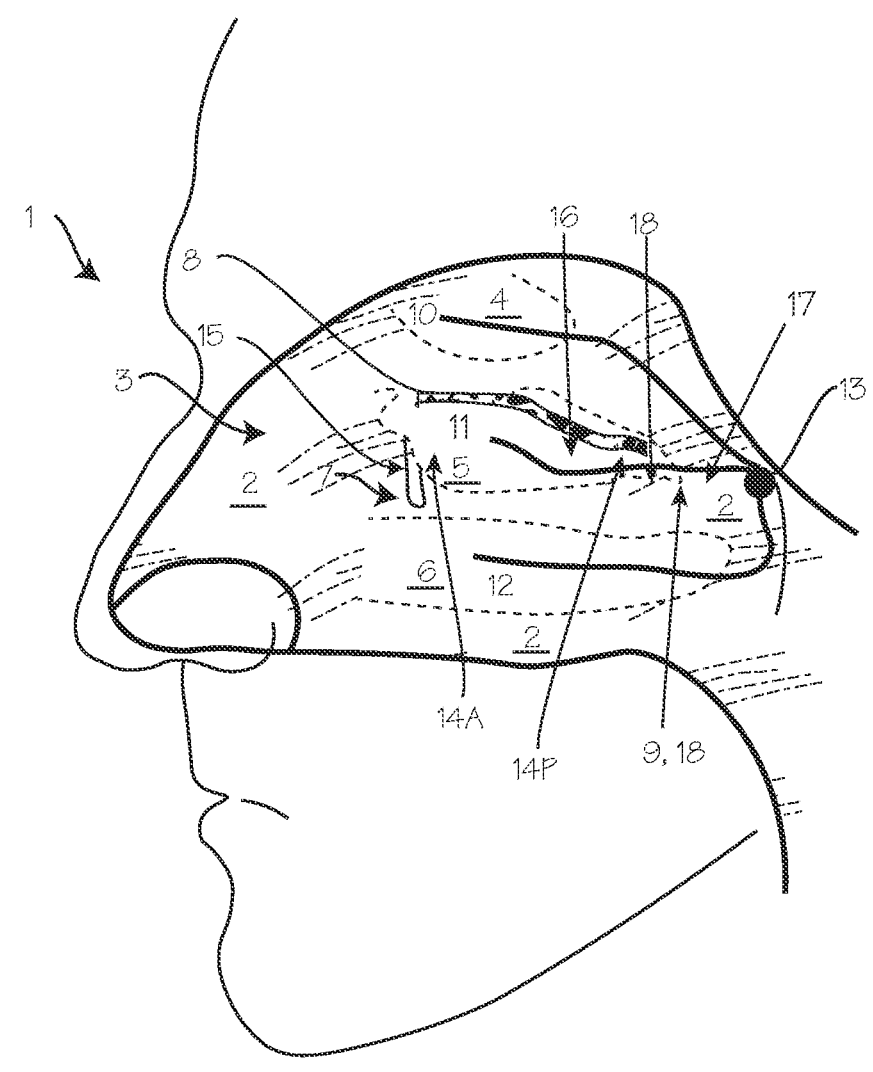
FIG. 1 is an internal lateral view of the nasal cavity showing the relevant nasal anatomy and the associated nerves within and near the targeted region of the lateral nasal wall.
Figure 2:
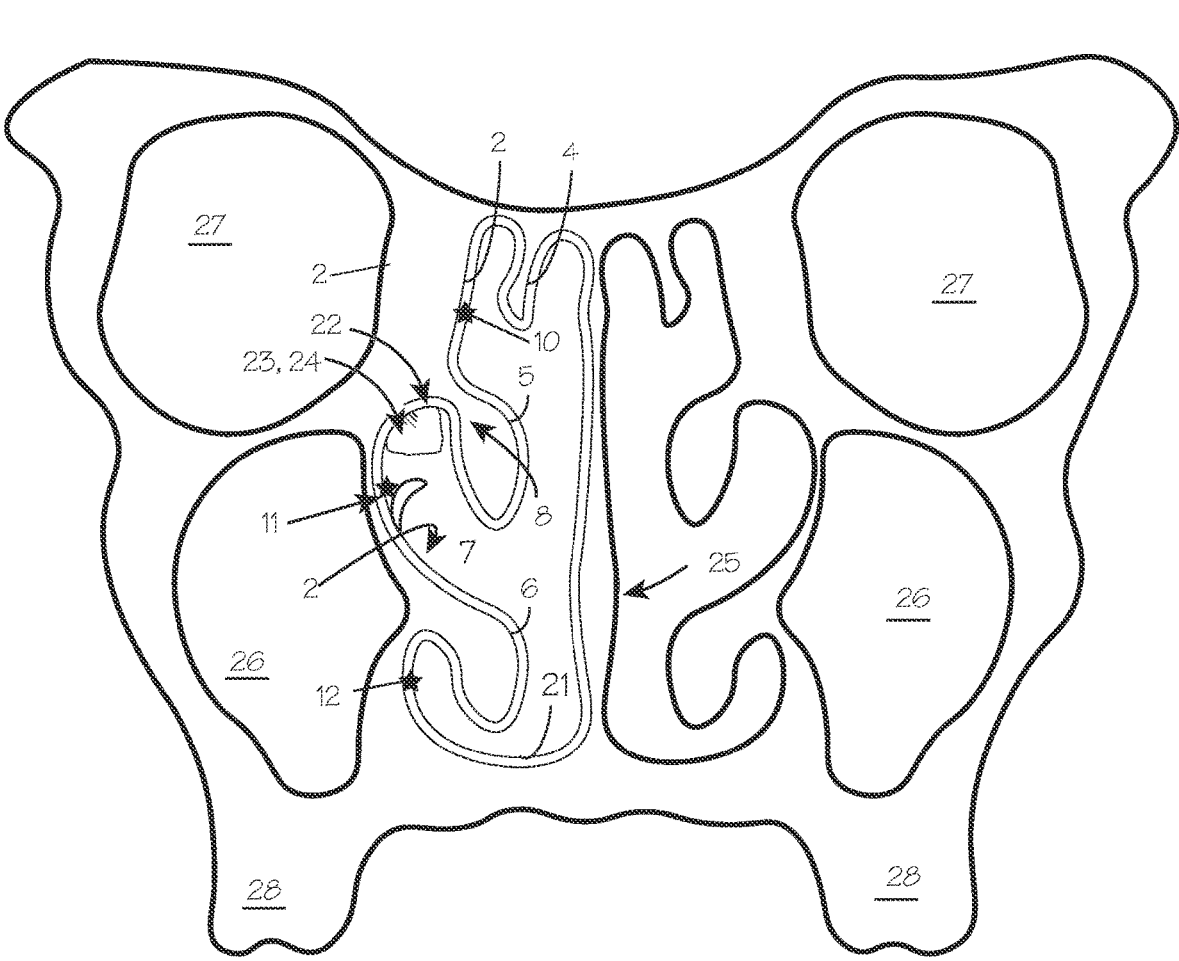
FIG. 2 is an anterior cross-sectional view of the nasal cavity showing the relevant nasal anatomy and the associated nerves within and near the targeted region of the lateral nasal wall.

FIG. 1 is a parasagittal view of a patient 1 and the nasal cavity lateral wall 2 within one side of the nasal cavity 3. The turbinates include a superior turbinate 4, a middle turbinate 5 and an inferior turbinate 6, running in an anterior-to-posterior orientation along the nasal cavity lateral wall 2. The turbinates are shown in phantom, to indicate that they are not in the same plane as the nasal cavity lateral wall 2. In this view, they are in front of the lateral wall (nearer the viewer). The turbinates hang down, like awnings, from the lateral wall. The turbinates, after extending medially from the nasal wall, drop downwardly. The turbinates are separated by passages, such as the middle meatus 7, which is a passage between the turbinate and the lateral wall 2 (that is, between the lateral surface of the depending portion of the middle turbinate and the medial surface of the lateral wall) and also under the middle turbinate and above the inferior turbinate. The bone of the middle turbinate, close to where the turbinate attaches to the bone of the lateral wall, is shown as item 8 (see FIG. 2), and the transition line or border between the turbinate and the lateral wall is referred to as the "attachment" of the turbinate. The turbinates meet the lateral wall at "attachments" at the inferior border, superior border, posterior end and anterior end of the turbinate. In this view of FIG. 1, the inferior attachments are behind (lateral to) the turbinates. A mucus membrane (which is shown in FIG. 2) covers the turbinates. A nub 9 of the posterior attachment is a rounded rib which depends downwardly from the posterior end of the middle turbinate, and comprises a thin terminal portion of the attachment. The lateral branches of the posterior nasal nerves include lateral branches 10, 11 and 12, innervating the lateral wall of the nasal cavity and the superior turbinate 4, middle turbinate 5, and the inferior turbinate 6, respectively. These posterior nasal nerves originate from the sphenopalatine ganglion 13 and run along the lateral nasal wall, lateral to the depending portions of the turbinates (behind them, in this view). These lateral branches of the posterior nasal nerves are responsible for the parasympathetic control of the nasal mucosa including the mucosa covering the turbinates, and these nerves are the target of the cryoablation to be achieved by the device of the following figures. These nerves are accessible to cryoablation in the area posterior to the anterior attachment 14A and anterior and posterior to the posterior attachment 14P of the middle turbinate. The uncinate process 15, which is a hook-shaped bony projection ridge running downwardly and posteriorly from the anterior end of the attachment of the middle turbinate toward the inferior turbinate, overlies other nerves involved in rhinitis and nasal obstruction. FIG. 1 illustrates several treatment zones from which the branch 11 posterior nasal nerve may be cryo-ablated. A first treatment zone 16 is located inferior to (lower than) the middle turbinate attachment 14, posterior to the uncinate process 15 and anterior to the posterior end of the attachment (identified as item 14P) of the middle turbinate, on the nasal cavity wall of the middle meatus. A second treatment zone 17 is the area superior to (above) the middle turbinate, and posterior to the posterior end of the middle turbinate, on the lateral wall of the nasal cavity. A third treatment zone 18 includes a nub 9 of the posterior attachment, which depends downwardly from the posterior end of the middle turbinate. 1920

FIG. 2 is an anterior cross-sectional view of the nasal cavity showing the relevant nasal anatomy and the associated nerves within and near the targeted region of the lateral nasal wall. This view shows the turbinates 4, 5 and 6 extending from the lateral wall 2 of the nasal cavity, and covered with a mucus membranes 21 and the middle meatus 7 between the middle turbinate and the inferior turbinate. The inferior attachment of the middle turbinate to the lateral wall is marked as item 22. The typical location of some branches of the posterior nasal nerve's 10, 11 and 12 are indicated, running through the mucus membranes lateral to the turbinates, and (2) running anterior to and posterior relative to the patient. FIG. 2 illustrates a fourth treatment zone 23 on a front facing surface 24 at the posterior end of the middle turbinate. This is the front facing surface of the "nub' at the posterior end of the middle turbinate, identified as item 9 in FIG. 1. Other landmarks in this view include the septum 25, the maxillary sinuses 26, and the eye sockets 27 and the upper jaw 2.

As shown in FIGS. 1 and 2, the turbinates extend from the lateral nasal wall medially (toward the septum) and inferiorly (downwardly) into the nasal cavity.

Figure 3:
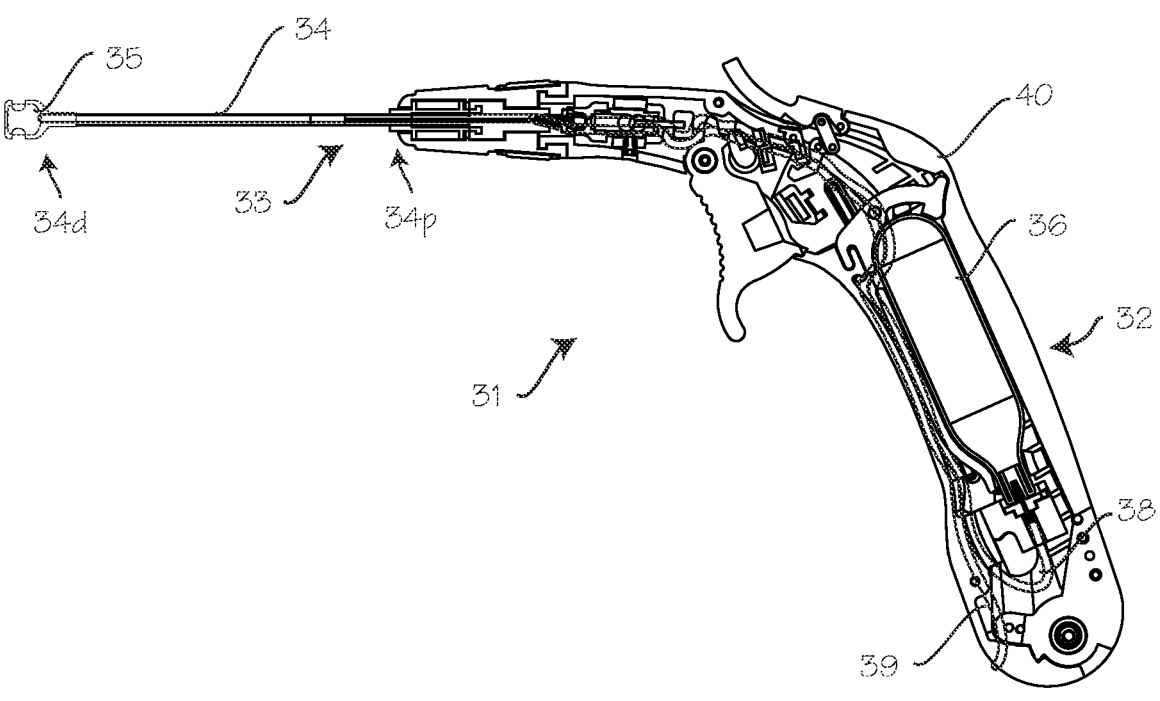
FIG. 3 illustrates the cryoablation system configured for ablating a posterior nasal nerve.
Figure 4:
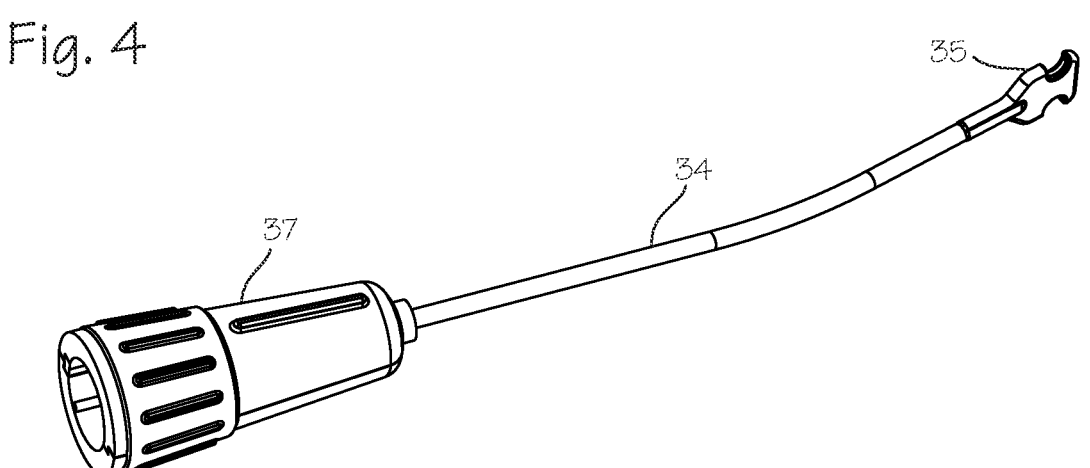
FIG. 4 illustrates the insertion portion of the cryoablation system of FIG. 2.

FIG. 3 illustrates a cryoablation system 31 configured for ablating a posterior nasal nerve. This system is preferably handheld, as shown, though it may be part of a robotically controlled system. As shown, the system includes a handle portion 32 and an insertion portion 33 extending distally from the handle portion. The insertion portion includes the shaft 34 with a cryoablation tip 35 disposed at the distal end of the shaft 34d. A cryogen reservoir in the form of a cartridge 36 containing any suitable cryogen (typically, liquid $CO_2$, Canisters of $N_2O$ (nitrous oxide), ethane, propane, methane or tetrafluoromethane (R14) may also be used. (Because the device is designed to use the liquid cryogen, rather than the gaseous cryogen, within the canister, the canister is held in fixed relationship to the cryoablation instrument, with the outlet pointing downward, establishing an up-and-down orientation for the device. In use, the cartridge which is disposed at a substantial angle relative to the cryoablation instrument and is disposed in an inclined position when the cryoablation instrument shaft is horizontally oriented.) Other cryogens and systems may be used, such as unpressurized liquid cryogen from a remote reservoir or gaseous cryogen such as argon delivered from a remote source (coupled with an expansion orifice opening into the cryoablation tip and using the Joule-Thomson effect for cooling). The insertion portion and shaft of the cryoablation system may be rigidly fixed to the handle portion or it may be a separable component, as shown in FIG. 4, releasably attachable to the handle portion at the proximal end of the shaft 34p through a quick release or screw-cap fitting 37, so that the handle portion may be reused with new, sterile insertion portions. Referring again to FIG. 3, the systems includes a cryogen supply line 38 communicating from the cartridge outlet in the handle, through the handle portion and shaft and into the cryoablation tip, and a cryogen exhaust line 39 communicating from the cryoablation tip, back through the shaft to exhaust used cryogen to atmosphere, at any point proximal to the tip, such as the proximal end 32p of the handle portion. The handle portion also includes a valve and trigger for operating the valve, to control flow of cryogen to the cryoablation tip, and a hinged cover 40 for entrapping the cartridge in the handle portion. The shaft 34 may be rigid (not easily bent), plastically deformable (it may bend, and remain bent), or resiliently deformable (bendable, and returning to initial configuration when released). The shaft may be straight, curved, or bent to accommodate passage of the shaft through the nostrils of the patient and along the turbinates. The handle portion may be configured as shown, configured to be held in an operator's hand, or it may be an attachment to a mechanical or robotic system configured to insert the insertion portion.

Figure 5:
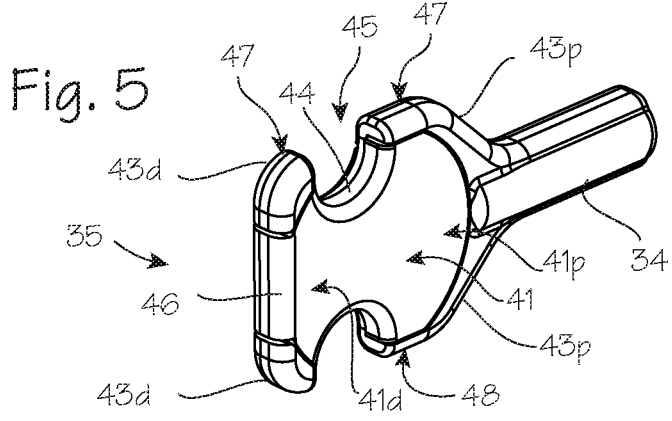
FIGS. 5 and 6 and 7 illustrates the cryoablation tip of the cryoablation system of FIG. 3.
Figure 6:
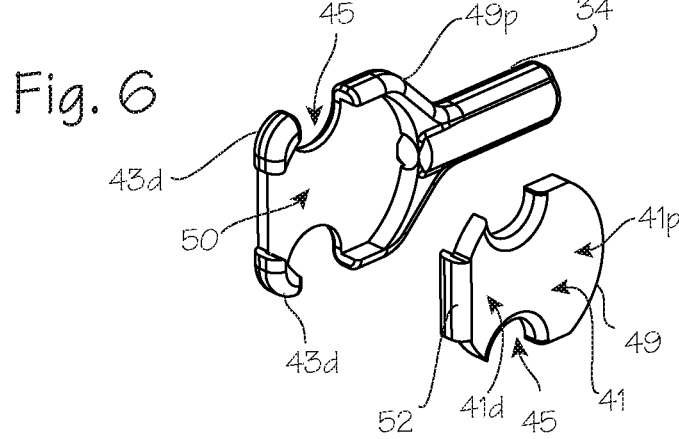

FIGS. 5 and 6 illustrates the cryoablation tip of the cryoablation system of FIG. 3.

As shown in FIG. 5, the cryoablation tip 35 is generally paddle-shaped, with broad, flat, overall rectangular outline (like a canoe paddle, or a pickleball paddle) with notches on the sides to create a metacentric outline. One broad side 41 of the cryoablation tip is highly thermally conductive. while the opposing broad side 42 of the cryoablation tip is highly thermally insulative (non-conductive). Distal corner portions 43d and proximal shoulder portions 43p of the side-edge surfaces of the cryoablation tip are also highly thermally insulative (non-conductive). Intermediate portions 44 of the side-edge surfaces (between the corners and shoulders) may be thermally conductive, and are configured as recesses or notches 45 in the side edge. A distal-most surface 46 of the cryoablation tip, between the insulative distal corner portions 43d, is highly conductive. As illustrated, the tip has a side edge 47, 48 on both sides of the tip, so a single insertion portion can be used to treat both the right and left sides of a patient. The insulative side 42 comprises a body including an insulative surface corresponding to the first broad surface.

The broad, flat conductive surface 41 is configured for application to, and contact with, the lateral nasal wall bordering the posterior middle meatus (the wall between the middle turbinate and the inferior turbinate, accessed through the passage running anterior-to-posterior between the middle and inferior turbinate), which overlies a branch of the posterior nasal nerve (typically). The broad, flat insulative surface 42 is not used for cryoablation, but may contact or oppose the under surfaces (the lateral surfaces) of the turbinates opposite the lateral wall and prevent ablation of those surfaces. The conductive surfaces 44 and the notches 45 are configured to receive and contact tissue of the nub 9 depending from the posterior end of the middle turbinate. These notches allow the surgeon to position the device for simultaneous ablation on the lateral nasal wall in the middle meatus (anterior to (in front of) the attachment of the middle turbinate) with the flat surface and also contact the posterior lateral nasal wall behind the middle turbinate. The combination of the flat conductive surface 41 and the conductive surfaces 44 in the notches 45 allows for simultaneous cryoablation of the area anterior to and posterior to the attachment of the middle turbinate. The inclusion of a notch on both sides of the cryoablation tip allow for use of the same insertion portion and cryoablation tip on both sides of a patient's nasal cavity. The cryoablation tip may be configured with a notch on only one side, which will require use of distinct left and right insertion portions while still achieving the benefits of the configuration of the cryoablation tip and its method of use. The conductive distal-most surface 46 is configured for application to, and contact with, the tissue where the inferior attachment of the middle turbinate inserts into the lateral nasal wall (especially advantageous to access this area which is typically tight and narrow and be difficult to access).

The flat conductive surface 41, surface of the notches 45 and the conductive distal-most surface 46 may comprise any highly thermally conductive material, including metals such as steel, brass, copper or aluminum. The opposing broad insulative side 42 may comprise any relatively thermally insulative material such as plastic, such as PPEK, or ceramic. These materials have widely disparate thermal conductivity, such that designating metals as high thermal conductivity and plastics and ceramics as low conductivity is sufficiently definite for artisans to reproduce the cryoablation tip. More specifically, the thermally conductive materials may preferably have a thermal conductivity in a high range of 10 W/m*K and above at cryogenic temperatures (preferably 300 W/m*K and above, with metal such as copper) and the thermally insulative materials may preferably have a thermal conductivity in the low range of 10 W/m*K and below (preferably in the low range of 1 (one) W/m*K and below, with materials such a PEEK or ePTFE (polytetrafluoroethylene) at cryogenic temperatures). For the purposes of this definition, "cryogenic temperatures" may fall in the range of −20° C. to −100° C., which is sufficiently cold to ablate the posterior nasal nerve through the overlying mucus membrane.

Figure 7:
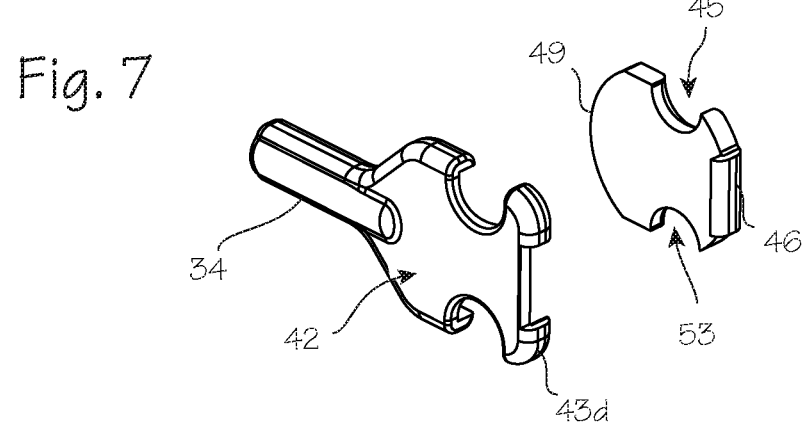

As shown in FIG. 6, the cryoablation tip may be formed in two (or more) pieces, with a first piece comprising a chamber 49 which is paddle shaped and a second piece comprising a cover 50 with a complimentary paddle shape and a recess configured to receive the chamber 49. The chamber 49 has an inlet for receiving cryogen from the supply line 38 and an outlet for exhaust of cryogen from the chamber through the exhaust line 39. It may be closed, without apertures other than the inlet and outlet, and may include apertures for exhaust of cryogen (such that the supply line is unnecessary). The chamber includes the notches 45 in the side edge, and the distal-most surface 46. The second piece may then comprise the cover 50 for one side of the chamber, with fingers extending from a flat panel shaped to match the chamber, with the fingers and flat panel shaped to create a space into which the chamber securely fits. FIG. 7 is a second view of the cryoablation tip 35, showing the highly thermally insulative side 42.

Though the preferred configuration of the cryoablation tip includes a closed chamber, covered by a second insulative piece, the two sides 42 and 41 may be configured to create a void between the portions, enclosed by the two portions, so that cryogen passing through into and out of the tip passes over the inner side of both the insulative portion and the conductive portion (with cryogenic cooling effect on tissue proximate the conductive portion and little if any cooling effect on tissue proximal the insulative portion). The notch surfaces may comprise walls depending from the conductive portion and corner portions extending from the insulative portion, which cooperate to form a closed chamber when assembled.

Figure 8:
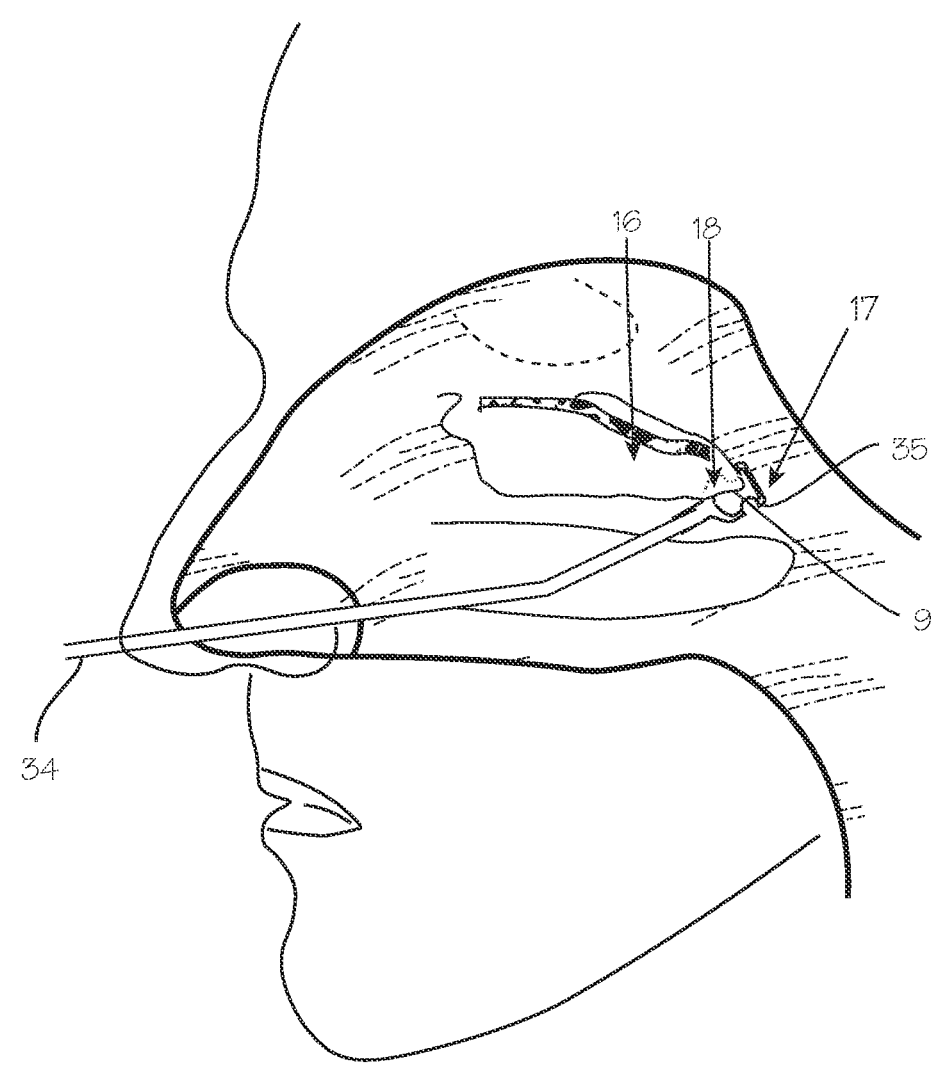
FIGS. 8, 9, and 10 illustrates use of the system.

FIG. 8 illustrates use of the system in a patient with a typical coarse of the posterior nasal nerve. In FIG. 8, the system has been assembled, with the cartridge installed in the handle and ready to supply cryogen to the cryoablation tip. A surgeon has inserted the insertion portion, with the cryoablation tip, through the nostril of a patient and deep within the nasal cavity, translating the cryoablation tip posteriorly through the meatus of the turbinate (in this illustration, the middle turbinate). The surgeon will position the cryoablation tip such that a proximal portion 41p of the flat broad conductive side is in contact with the lateral wall of the nasal cavity (specifically, a lateral wall of the middle meatus) (the first treatment zone 16 mentioned above), and the non-conductive side opposes the lateral tissue of the turbinate, and a distal portion 41d of the flat broad conductive side is in contact with the second treatment zone 17 in the area superior to (above) the middle turbinate, and posterior to the posterior end of the middle turbinate, on the lateral wall of the nasal cavity, and one of the notches receives the nub 9 of the posterior attachment in the third treatment zone (the other notch is used on the opposite side of the nasal cavity). The target posterior nasal nerve, or branches of the posterior nasal nerve, pass through the portion of the turbinate received with the notch and proximate the flat surface of the conductive side (in the typically anatomy). The preferred method of operation includes place of the cryoablation tip such that, as shown, the flat broad conductive surface contacts treatment zone 1, 2 and 3 simultaneously, such that a single application of cryogen while the cryoablation tip is positioned as shown is effective to ablate the posterior nasal nerve and thereby treat rhinitis or nasal congestion.

Figure 9:
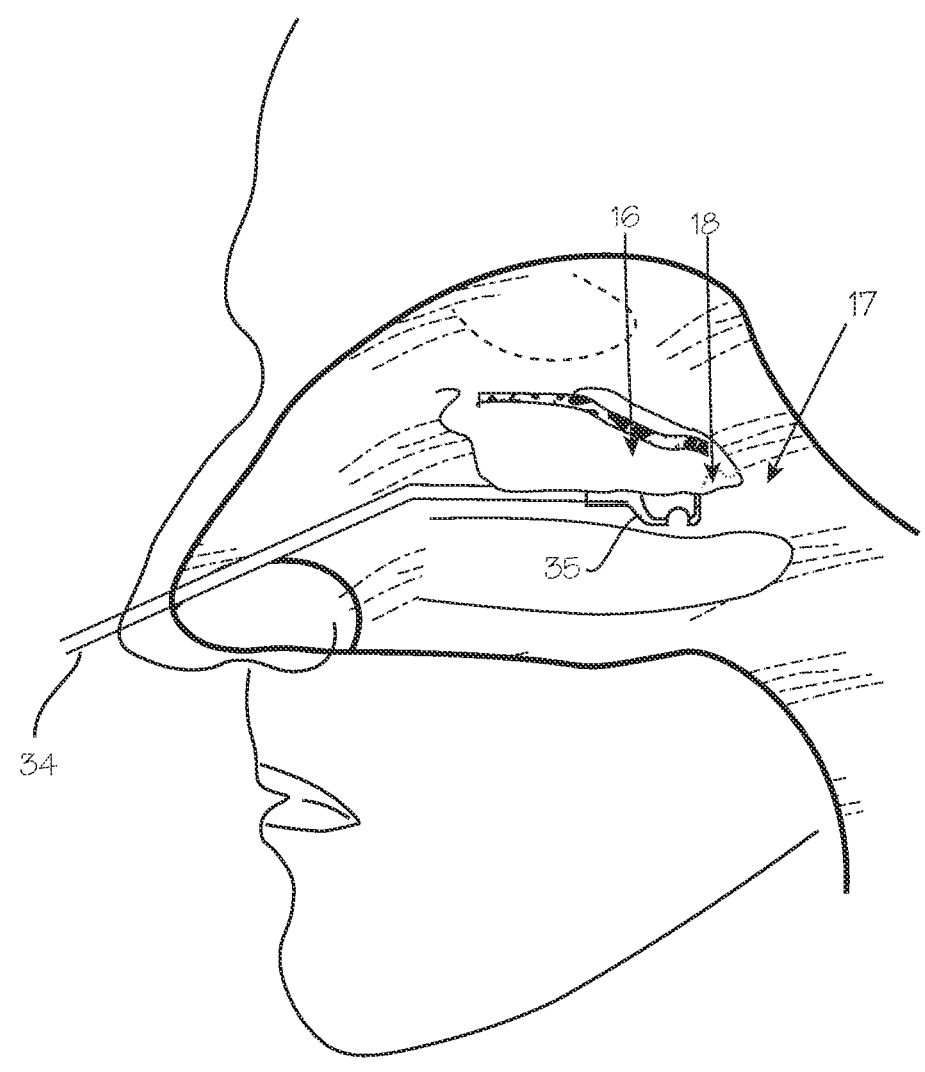
Figure 10:
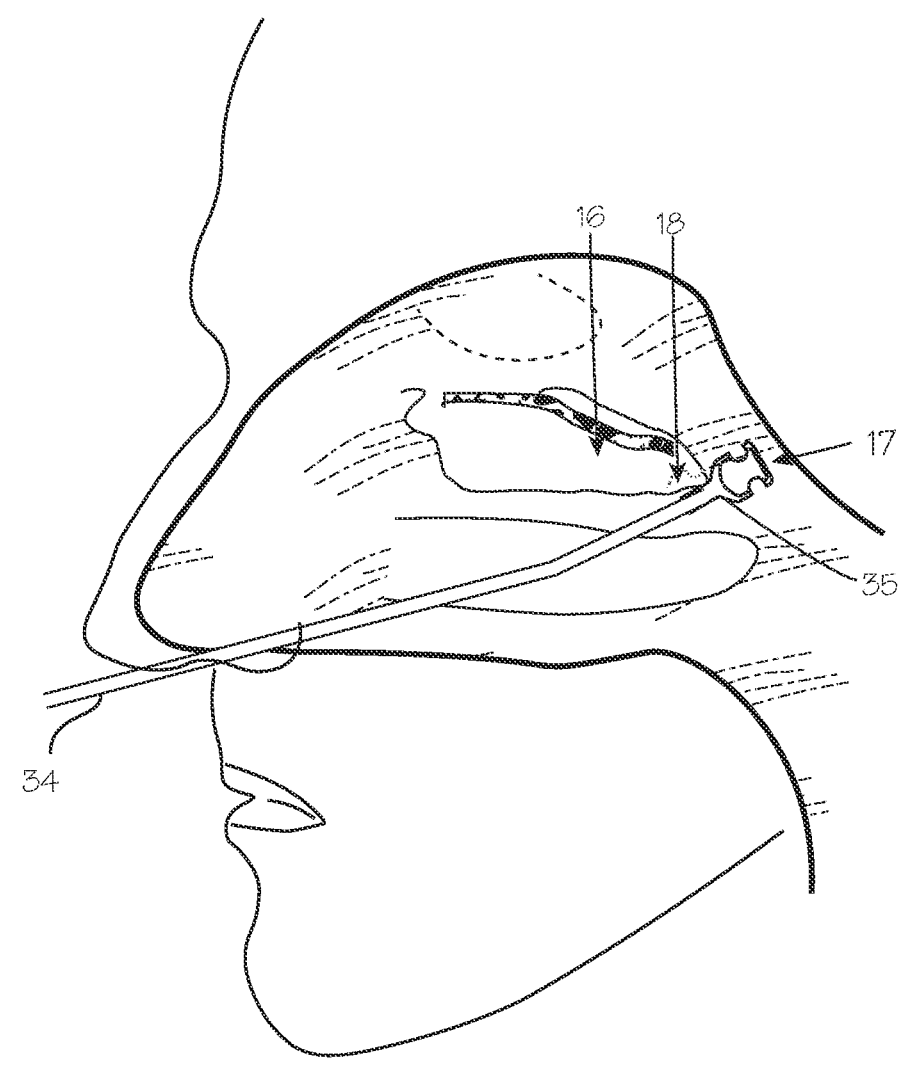

FIG. 9 illustrates use of the cryoablation system to cryoablate the posterior nasal nerve in the first treatment zone 16, which includes the lateral wall of the middle meatus with the broad flat thermally conductive surface of the cryoablation tip 35, without simultaneously treating the other treatment zones. FIG. 10 illustrates use of the cryoablation system to cryoablate the posterior nasal nerve in second treatment zone 17, which includes the lateral wall posterior to and superior to the posterior end of the middle turbinate with the broad flat thermally conductive surface of the cryoablation tip, without simultaneously treating the other treatment zones.

Figure 11:
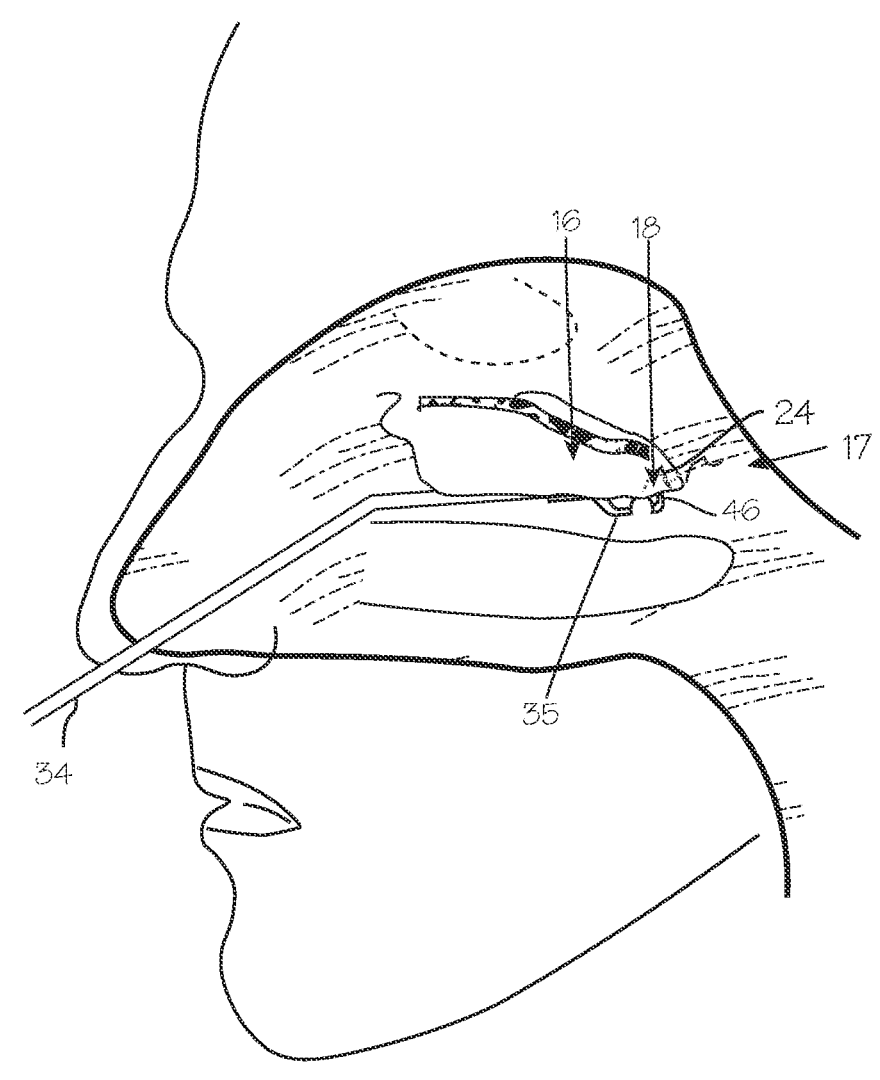
FIG. 11 shows the cryoablation tip and surrounding anatomy when in its target position.

FIG. 11 illustrates use of the cryoablation system to cryoablate the posterior nasal nerve in a fourth treatment zone, which includes front facing surface 24 of the nub 9 at the posterior end of the middle turbinate. The cryoablation tip 35 and shaft 34 are shown in the Figure, depicting approach and application of the distal-most surface 46 (see FIG. 5) to the front facing surface 24 of the nub 9 at the posterior end of the middle turbinate. While applying the distal-most surface 46, the thermally conductive side of the cryoablation tip may or may not be pressed against the lateral wall of the middle meatus. If the thermally conductive side of the cryoablation tip is pressed against the lateral wall of the meatus while the distal-most surface 46 is pressed against the lateral wall of the middle meatus, the surgeon may apply cryogenic cooling to both the first and fourth treatment zones simultaneously.

As demonstrated by FIGS. 9, 10 and 11, the several treatment zones may be treated one at a time, rather than simultaneously, while still being treated in the intra-operative time frame, and without the need to remove the cryoablation tip from the nasal cavity, thus reducing the procedure time and eliminating the discomfort for the patient arising from repeated removal and re-insertion of the insertion portion. Though the notch surfaces are preferably thermally conductive, they may be thermally insulative in an embodiment which allows for use in a method of treatment including placement as indicated in FIG. 9, and simultaneously treating zone 1 and zone 2 (the lateral wall anterior to the nub and the lateral wall posterior to the nub) by applying cryoablative cooling without applying cryoablative cooling to zone 3 (the nub).

Application of cryogen for a few seconds (about 30-120 seconds) to cool the posterior nasal nerve and overlying tissue to cryoablative temperatures of –20 to –100° C. should be sufficient to ablate and disrupt the posterior nasal nerve, sufficient to result in reduction in the symptoms of chronic rhinitis and nasal congestion, without unduly injuring the mucus membrane in the treatment zones.

In use, a surgeon will insert the cryoablation tip and distal end of the insertion portion into the nasal cavity of a patient, and position the thermally conductive side against the lateral nasal wall in one of the several treatment zones, with the insulative second broad side 42 facing the lateral surface of the middle turbinate, and operate the system to cool those portions to ablate the posterior nasal nerve. The surgeon preferably places the cryoablation tip such that the thermally conductive side of the tip contacts the lateral wall in the middle meatus just anterior to the posterior end of the middle turbinate and, at the same time also contacts the lateral wall at a location anterior the posterior end of the middle turbinate (and, depending on the anatomy encountered in a particular patient, superior to the posterior end of the middle turbinate). The surgeon may also place the cryoablation tip such that the nub at the posterior end of the middle turbinate is disposed within a notch on the side of the cryoablation tip. With the cryoablation tip in place, the surgeon will operate the system to initiate supply of cryogen to supply the cryogen to the cryoablation tip to ablate the posterior nasal nerve along its expected course, including the first and second and preferably the third target zone (the nub). The method may include simultaneous cryoablation in the first zone and second zone (without necessarily cryoablating the third zone). This method may be augmented by positioning the conductive distal surface against the surface of target zone 4. The method may also include placing the cryoablation tip in one zone at a time, first in any one of the zones, then in any one of the remaining zones, or all four of the treatment zones, and initiating cryoablation separately at each zone, or applying cryoablation to a single zone (such as the first treatment zone or fourth treatment zone) without applying cryoablation to the remaining zones. These methods are performed without cooling or cryoablating other areas of the lateral wall, the lateral or medial surfaces of the middle turbinate, the area of the ganglion 13 or other area, by placing the cryoablation tip such that the thermally insulative second broad side 42 is located proximate to those structures (for example, the lateral or medial surfaces of the middle turbinate) and/or the thermally conductive first broad side 41 is placed to avoid contact with those structures (for example, the ganglion 13 or other area).

With the method as describe in mind, the system and the structure of the cryoablation tip can be further summarized: The cryoablation system 31 is configured for ablating a posterior nasal nerve 11 which enervates a lateral nasal wall 2 of a patient. The system comprises a handle portion 32 and an insertion portion 33 extending distally from the handle portion 32. The insertion portion comprises a shaft 34 having a distal end 34*d* and a proximal end 34*p*, with a cryoablation tip 35 disposed at the distal end of the shaft, and a cryogen reservoir 36 configured for delivery of cryogen to the cryoablation tip.

The cryoablation tip 35 is generally paddle-shaped, with a broad, flat, overall rectangular outline and a thermally conductive first broad side 41 and a thermally insulative second broad side 42, with first side edge 47 and second side edge 48 between the first broad surface and the second broad surface and a first notch 45 in the first side edge 47, whereby said cryoablation tip is configured for placement in the nasal cavity of a patient such that (1) a proximal portion 41*p* of the thermally conductive first broad side 41 may be disposed against a first treatment zone 16 located inferior to (lower than) the middle turbinate attachment 14, posterior to the uncinate process 15 and anterior to the posterior end of the attachment, while at the same time (2) a distal portion 41*d* of the thermally conductive first broad side 41 may be disposed against a second treatment zone 17 comprising an area superior to (above) the middle turbinate, and posterior to the posterior end of the middle turbinate, on the lateral wall of the nasal cavity while at the same time (3) the first notch 45 may be disposed in a third treatment zone, comprising a nub 9 of a posterior attachment of a middle turbinate.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A cryoablation system (31) configured for ablating a posterior nasal nerve (11) enervating a lateral nasal wall (2) of a patient, said system comprising a handle portion (32) and an insertion portion (33) extending distally from the handle portion (32), said insertion portion comprising a shaft (34) having a distal end (34*d*) and a proximal end (34*p*), with a cryoablation tip (35) disposed at said distal end of the shaft, and a cryogen reservoir (36) configured for delivery of cryogen to the cryoablation tip, wherein:

the cryoablation tip (35) is paddle-shaped, with a broad, flat, overall rectangular outline and a thermally conductive first broad side (41) and a thermally insulative second broad side (42), with a first side edge (47) and a second side edge (48) between the first broad side and the second broad side and a first notch (45) in the first side edge (47), whereby said cryoablation tip is configured for placement in a nasal cavity of the patient such that:

(1) a proximal portion (41*p*) of the thermally conductive first broad side (41) is configured to be disposed against a first treatment zone (16) located inferior to a middle turbinate attachment (14) of a middle turbinate (5), posterior to an uncinate process (15) and anterior to a posterior end (14*p*) of the middle turbinate attachment (14); while at the same time, (2) a distal portion (41*d*) of the thermally conductive first broad side (41) is disposed against a second treatment zone (17) comprising an area superior to the middle turbinate (5), and posterior to a posterior end of the middle turbinate, on the lateral nasal wall (2) of the nasal cavity; while at the same time, (3) the first notch (45) is disposed in a third treatment zone comprising a nub (9) at the posterior end (14*p*) of the middle turbinate attachment (14).

2. The cryoablation system of claim 1, wherein the first notch (45) has a side-edge surface, and the side-edge surface of the first notch (45) is thermally conductive, and configured to apply cryogenic cooling to the nub.

3. The cryoablation system of claim 1, wherein the cryoablation tip further comprises a thermally conductive distally facing surface configured for application to a fourth treatment zone on a front facing surface of the nub at the posterior end of the middle turbinate.

4. The cryoablation system of claim 1, further comprising a second notch (45) in the second side edge (48).

5. A method of treating rhinitis in a patient, said method comprising:

providing the cryoablation system of claim 1;

inserting the cryoablation tip and the distal end of the insertion portion into the nasal cavity of the patient, and positioning the cryoablation tip such that:

the proximal portion of the thermally conductive first broad side (41) is disposed against the first treatment zone (16);

the distal portion of the thermally conductive first broad side (41) is disposed against the second treatment zone (17); and the first notch is disposed in the third treatment zone, with the nub (9) of the posterior attachment of the middle turbinate intruding into the first notch; and initiating supply of cryogen to the cryoablation tip to simultaneously cryoablate the posterior nasal nerve proximate the first treatment zone and second treatment zone.

6. The method of claim 5, wherein:

the first notch (45) has a side-edge surface, and the side-edge surface of the first notch (45) is thermally conductive, and configured to apply cryogenic cooling to the nub; and the method further comprises:

locating the cryoablation tip such that the side-edge surface of the first notch (45) contacts a surface of the nub, whereby initiation of supply of cryogen to the cryoablation tip applies cryogenic cooling to the nub while simultaneously cryoablating the posterior nasal nerve proximate the first treatment zone and second treatment zone.

7. The method of claim 5, wherein:

the nub is characterized by an anterior facing surface; and the cryoablation tip further comprises a thermally conductive distally facing surface configured for application to a fourth treatment zone on the anterior facing surface of the nub at the posterior end of the middle turbinate;

and the method further comprises:

applying the thermally conductive distally facing surface to the anterior facing surface of the nub; and initiating supply of cryogen to the cryoablation tip to cryoablate the posterior nasal nerve proximate the fourth treatment zone on the anterior facing surface of the nub at the posterior end of the middle turbinate.

8. The method of claim 5, wherein:

cryoablation of the first treatment zone or second treatment zone is accomplished without cooling or cryoablating other areas of the lateral nasal wall, a medial surface of the middle turbinate, or an area of a ganglion (13).

9. A method of treating rhinitis in a nasal cavity of a patient, said method comprising:

providing a cryoablation system comprising:

a handle portion (32) and an insertion portion (33) extending distally from the handle portion (32), said insertion portion comprising a shaft (34) having a distal end (34*d*) and a proximal end (34*p*), with a cryoablation tip (35) disposed at said distal end of the shaft, and a cryogen reservoir (36) configured for delivery of cryogen to the cryoablation tip, wherein:

the cryoablation tip (35) is paddle-shaped, having a thermally conductive first broad side (41) and a thermally insulative second broad side (42), whereby said cryoablation tip is configured for placement in the nasal cavity of the patient such that:

(1) the thermally conductive first broad side (41) is configured to be disposed against a first treatment zone (16) located inferior to a middle turbinate attachment (14) of a middle turbinate (5) of the patient, posterior to an uncinate process (15) and anterior to a posterior end of the middle turbinate attachment (14); while at the same time, (2) the thermally insulative second broad side (42) may be located proximate a lateral surface of the middle turbinate (5);

inserting the cryoablation tip and distal end of the insertion portion into the nasal cavity of the patient, and positioning the cryoablation tip such that:

the thermally conductive first broad side (41) is disposed against the first treatment zone (16) and the thermally insulative second broad side (42) is facing the lateral surface of the middle turbinate; and initiating supply of cryogen to the cryoablation tip to cryoablate a posterior nasal nerve proximate the first treatment zone.

10. A cryoablation system (31) configured for ablating a posterior nasal nerve (11) enervating a lateral nasal wall (2) of a patient, said system comprising a handle portion (32) and an insertion portion (33) extending distally from the handle portion (32), said insertion portion comprising a shaft (34) having a distal end (34*d*) and a proximal end (34*p*), with a cryoablation tip (35) disposed at said distal end of the shaft, and a cryogen reservoir (36) configured for delivery of cryogen to the cryoablation tip, wherein:

the cryoablation tip (35) is paddle-shaped, with a broad, flat, overall rectangular outline and a thermally conductive first broad side (41) with a first broad side proximal portion (41*p*) and a first broad side distal portion (41*d*) and a thermally insulative second broad side (42), said cryoablation tip also having a first side edge (47) and a second side edge (48) between the first broad side and the second broad side and a first notch (45) in the first side edge (47), whereby said cryoablation tip is configured for placement in a nasal cavity of the patient, and wherein said proximal portion (41*p*), said distal portion (41*d*), and said first notch (45), are located on the cryoablation tip relative to each other such that the cryoablation tip (35) is positionable within the nasal cavity, with;

(1) the proximal portion (41p) of the thermally conductive first broad side (41) disposed against a first treatment zone (16) located inferior to a middle turbinate attachment (14) of a middle turbinate (5) of the patient, posterior to an uncinate process (15) and anterior to a posterior end (14p) of the middle turbinate attachment (14);

(2) the distal portion (41d) of the thermally conductive first broad side (41) disposed against a second treatment zone (17) comprising an area superior to the middle turbinate (5), and posterior to the posterior end (14p) of the middle turbinate attachment (14), on the lateral nasal wall (2) of the nasal cavity; and (3) the first notch (45) disposed in a third treatment zone comprising a nub (9) at the posterior end (14p) of the middle turbinate attachment (14).

11. A cryoablation system (31) configured for ablating a posterior nasal nerve (11) enervating a lateral nasal wall (2) of a patient, said system comprising a handle portion (32) and an insertion portion (33) extending distally from the handle portion (32), said insertion portion comprising a shaft (34) having a distal end (34d) and a proximal end (34p), with a cryoablation tip (35) disposed at said distal end of the shaft, and a cryogen reservoir (36) configured for delivery of cryogen to the cryoablation tip, wherein:

the cryoablation tip (35) is paddle-shaped, with a broad, flat, overall rectangular outline and a thermally conductive first broad side (41) with a first broad side proximal portion (41p) and a first broad side distal portion 41 (d) and a thermally insulative second broad side (42), said cryoablation tip also having a first side edge (47) and a second side edge (48) between the first broad side and the second broad side and a first notch (45) in the first side edge (47), whereby said cryoablation tip is configured for placement in a nasal cavity of the patient; wherein the first notch (45) is configured to receive a nub (9) of a posterior attachment of a middle turbinate when:

(1) the proximal portion (41p) of the thermally conductive first broad side (41) is disposed against a first treatment zone (16) located inferior to a middle turbinate attachment (14), posterior to an uncinate process (15) and anterior to a posterior end of the posterior attachment of the middle turbinate; and, at the same time, (2) a distal portion (41d) of the thermally conductive first broad side (41) is disposed against a second treatment zone (17) comprising an area superior to the middle turbinate, and posterior to the posterior end of the posterior attachment of the middle turbinate, on the lateral nasal wall (2) of the nasal cavity.

* * * * *